(12) United States Patent
Bitdinger et al.

(10) Patent No.: US 6,648,859 B2
(45) Date of Patent: Nov. 18, 2003

(54) DISPOSABLE, PRE-FILLED DRUG CARTRIDGE

(75) Inventors: Ralf V. Bitdinger, New York, NY (US); Katherine Birkland, Wayne, NJ (US)

(73) Assignee: Becton Dickinson and Company, Franklin Lakes, NJ (US)

(*) Notice: Subject to any disclaimer, the term of this patent is extended or adjusted under 35 U.S.C. 154(b) by 57 days.

(21) Appl. No.: 09/932,043

(22) Filed: Aug. 17, 2001

(65) Prior Publication Data

US 2003/0109834 A2 Jun. 12, 2003

Related U.S. Application Data

(63) Continuation of application No. 09/308,466, filed on Aug. 26, 1999, now abandoned, which is a continuation-in-part of application No. 08/939,776, filed on Sep. 29, 1997, now abandoned.

(51) Int. Cl.[7] .................................................. A61M 5/00
(52) U.S. Cl. ....................................... 604/232; 604/218
(58) Field of Search ................................. 604/218, 232, 604/233, 234, 235, 181, 187, 192, 207–211

(56) References Cited

U.S. PATENT DOCUMENTS

| 4,628,969 A | 12/1986 | Jurgens, Jr. et al. |
| 4,718,463 A | 1/1988 | Jurgens, Jr. et al. |
| 5,207,983 A | 5/1993 | Liebert et al. |
| 5,250,037 A | 10/1993 | Bitdinger |
| 5,279,585 A | 1/1994 | Balkwill |
| 5,279,586 A | 1/1994 | Balkwill |
| 5,373,684 A | 12/1994 | Vacca |
| 5,519,984 A | 5/1996 | Beussink et al. |
| 5,531,255 A | 7/1996 | Vacca |
| 5,542,760 A | 8/1996 | Chanoch et al. |
| 5,549,575 A | 8/1996 | Giambattista et al. |
| 5,569,214 A | 10/1996 | Chanoch |
| 5,582,598 A | 12/1996 | Chanoch |
| 5,645,534 A | 7/1997 | Chanoch |
| 5,667,495 A | 9/1997 | Bitdinger et al. |
| 5,674,204 A | * 10/1997 | Chanoch ..................... 604/211 |
| 5,725,508 A | 3/1998 | Chanoch et al. |
| 5,769,824 A | 6/1998 | Hjertman et al. ........... 604/143 |
| 5,931,817 A | 8/1999 | Nguyen et al. |

FOREIGN PATENT DOCUMENTS

WO 9413328 6/1994

* cited by examiner

Primary Examiner—Long V. Le
Assistant Examiner—Ann Y. Lam
(74) Attorney, Agent, or Firm—Hoffmann & Baron, LLP

(57) ABSTRACT

This invention relates to a drug cartridge assembly for use with a reusable body assembly of a medication delivery pen. The drug cartridge is disposable and is in the form of a single integral unit having a generally tubular barrel. Medication is pre-filled into the drug cartridge and is retained therein by an elastomeric stopper or plunger. The plunger is in sliding fluid-tight engagement with a tubular wall of the barrel. A proximal end of the tubular barrel is configured for interconnecting the drug cartridge with a pen body assembly and a distal end of the tubular barrel is configured to securely but releasably engage a needle cannula assembly.

7 Claims, 8 Drawing Sheets

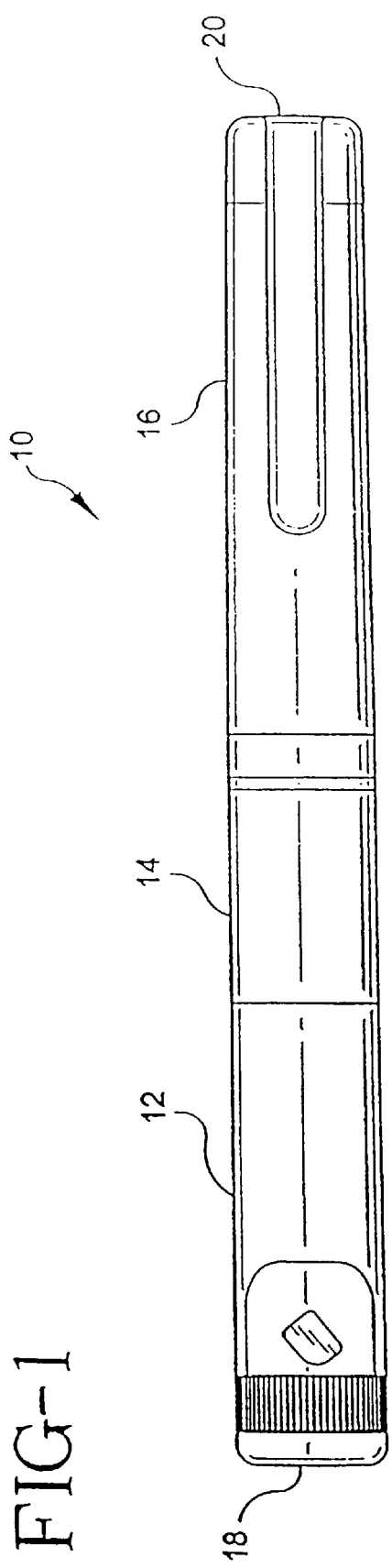
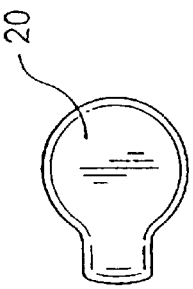
FIG-1
FIG-1A

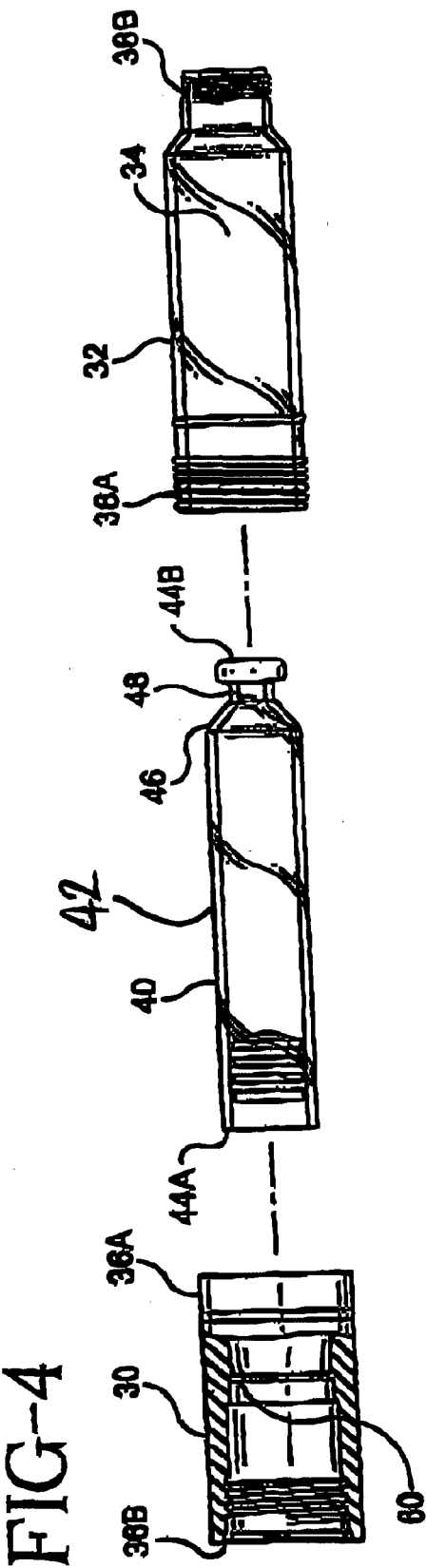
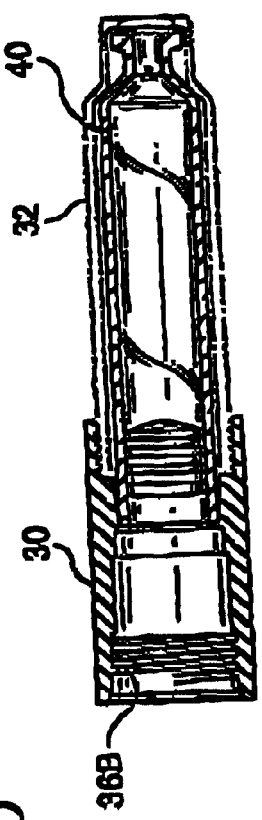
FIG-4
FIG-5

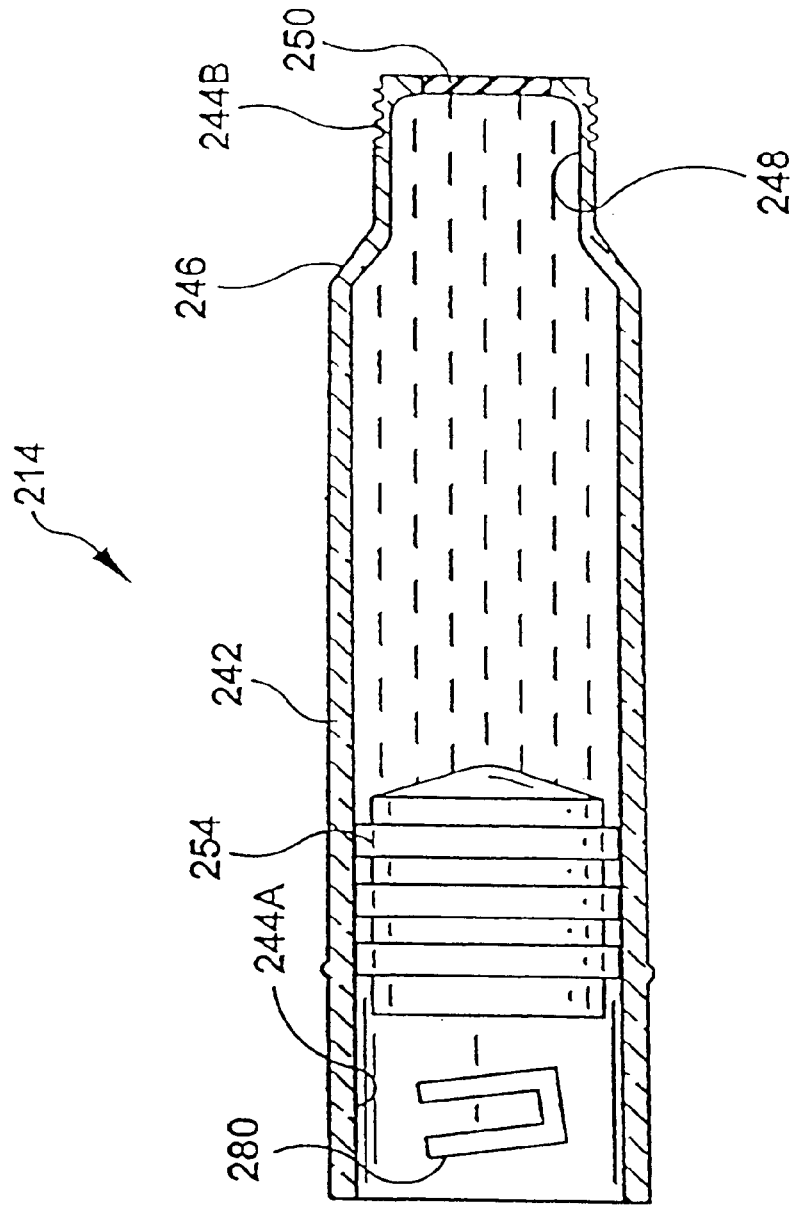
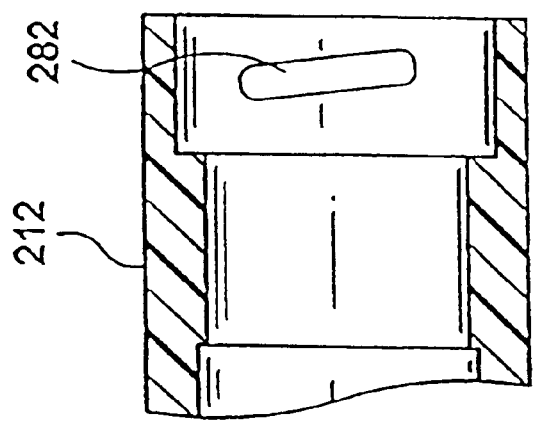
FIG-7

DISPOSABLE, PRE-FILLED DRUG CARTRIDGE

RELATED APPLICATION

The subject application is a continuation application of U.S. application Ser. No. 09/308,466, which was filed on Aug. 26, 1999, now abandoned, and is in turn a continuation-in-part of U.S. application Ser. No. 08/939,776, filed on Sep. 29, 1997, now abandoned.

FIELD OF THE INVENTION

The present invention generally relates to drug delivery devices, and more specifically relates to disposable, pre-fillable drug cartridge for use with a reusable body portion of an injection device for injecting drugs or medicaments into patients which are commonly known in the field as pens.

BACKGROUND OF THE INVENTION

Hypodermic syringes are used to deliver selected doses of medication to patients. The prior hypodermic syringe includes a syringe barrel having opposed proximal and distal ends. A cylindrical chamber wall extends between the ends and defines a fluid receiving chamber. The proximal end of the syringe barrel is substantially open and receives a plunger in sliding fluid tight engagement. The distal end of the syringe barrel includes a passage communicating with the chamber. A needle cannula may be mounted to the distal end of the syringe barrel, such that the lumen of the needle cannula communicates with the passage and the chamber of the syringe barrel. Movement of the plunger in a proximal direction draws fluid through the lumen of the needle cannula and into the chamber. Movement of the plunger in a proximal-to-distal direction urges fluid from the chamber and through the lumen of the needle cannula.

Medication to be injected with the prior hypodermic syringe often is stored in a vial having a pierceable elastomeric seal. Medication in the vial is accessed by piercing the elastomeric seal with the needle cannula. A selected dose of the medication may be drawn into the chamber of the syringe barrel by moving the plunger a selected distance in a proximal direction. The needle cannula may be withdrawn from the vial, and the medication may be injected into a patient by moving the plunger in a distal direction.

Some medication, such as insulin is self-administered. The typical diabetes patient will require injections of insulin several times during the course of a week or day. The required dose of insulin will vary from patient to patient, and for each patient may vary during the course of the day and from day to day. Usually, each diabetes patient will establish a regimen that is appropriate for his or her own medical condition and for his or her lifestyle. The regimen typically includes some combination of a slow or medium acting insulin and a faster acting insulin. Each of these regimens may require the diabetes patient to periodically self-administer insulin in public locations, such as places of employment or restaurants. The required manipulation of the standard hypodermic syringe and vial can be inconvenient and embarrassing in these public environments. Examples of syringes are described in U.S. Pat. Nos. 5,250,037 (Bitdinger) and 5,667,495 (Bitdinger), and an example of a filler for mixing insulins is described in U.S. Pat. No. 5,542,760 (Chanoch), the disclosures of which are hereby incorporated by reference in their entirety.

Medication delivery pens have been developed to facilitate the self-administration of medication. An example of one such medication delivery pen is described in U.S. Pat. No. 5,279,585 (Balkwill), which includes a vial holder into which a vial of insulin or other medication may be received, the disclosure of which is hereby incorporated by reference in its entirety. The vial holder is an elongate generally tubular structure with proximal and distal ends. The distal end of the vial holder includes mounting means for engaging a double-ended needle cannula. The proximal end also includes mounting means for engaging a driver and dose setting apparatus as explained further below. A disposable vial for use with the vial holder includes a distal end having a pierceable elastomeric seal that can be pierced by one end of a double-ended needle cannula. The proximal end of this vial includes a plunger slidably disposed in fluid tight engagement with the cylindrical wall of the vial. This medication delivery pen is used by inserting the vial of medication into the vial holder. A pen body then is connected to the proximal end of the vial holder. The pen body includes a dose setting apparatus for designating a dose of medication to be delivered by the pen and a driving apparatus for urging the plunger of the vial distally for a distance corresponding to the selected dose. Other examples of pens are described in U.S. Pat. Nos. 5,645,534 (Chanoch), 5,582,598 (Chanoch) and 5,569,214 (Chanoch), the disclosure of which are hereby incorporated by reference in their entirety.

The user of the pen mounts a double-ended needle cannula to the distal end of the vial holder such that the proximal point cannula of the needle cannula pierces the elastomeric seal on the vial as described, for example, in U.S. Pat. No. 5,549,575 (Giambattista et. al.), the disclosure of which is hereby incorporated by reference in its entirety. The user then selects a dose and operates the pen to urge the plunger distally to deliver the selected dose. The user then removes and discards the needle cannula, and keeps the medication delivery pen in a convenient location for the next required medication administration. The medication in the vial will become exhausted after several such administrations of medication. The user then separates the vial holder from the pen body. The empty vial may then be removed and discarded. A new vial can be inserted into the vial holder, and the vial holder and pen body can be reassembled and used again as explained above.

The above described reusable medication delivery pen is effective and much more convenient for self-administration of medication than the typical hypodermic syringe and separate medication vial. However, it has been found that there is a need for additional features and improvements for such a medication delivery pen. For example, with the increased use of pens for self-injection of drugs other than insulin, there is a need to prevent cross-use of insulin pens with other drugs and/or cross-use of drug cartridges with other pens. The problems associated with cross-use could also pose a potential hazard, where the dose dials of the pens are different, which might result in the administration of the wrong dosage of the drug. This is particularly hazardous where an overdose of insulin could lead to hypoglycemia and ER treatment.

Thus, there has been a need for a pen as well as a drug cartridge assembly, which would eliminate the problems and limitations associated with the prior devices discussed above, most significant of the problems being cross-use of the pen with other drug cartridge assemblies and/or cross-use of the drug cartridge assembly with other pens.

SUMMARY OF THE INVENTION

In contrast to the prior devices discussed above, it has been found that a pen particularly suited for use in reducing or otherwise eliminating cross-use can be constructed in accordance with the present invention. Specifically, the pen and the drug cartridge assembly of the present invention are keyed, i.e., they have a connection interface which mechanically prevents the cross-use of cartridge assemblies among designated pens by, for example, using matching threads, bayonets or snap fits on the pen and the holding sleeve of the drug cartridge assembly. Also, the cartridge assembly can have an embedded drug cartridge, not readily separable from each other.

Another object of the present invention is to improve the design of the drug cartridge and holder sleeve so that they are a single integral unit for containing the drug, with a rubber septum for multiple needle penetrations along with a standard thread to attach the pen needle. On the far end of the pen needle thread, a connection interface prevents connection to pens other than the one for which use of the drug container is designed. In this way, the drug cartridge assembly will have minimal dead space and an insert molded rubber septum.

BRIEF DESCRIPTION OF THE DRAWINGS

The various features, objects, benefits, and advantages of the present invention will become more apparent upon reading the following detailed description of the preferred embodiment(s) along with the appended claims in conjunction with the drawings, wherein like reference numerals identify corresponding components, and:

FIG. 1 is a top view of the injection pen of the present invention, with FIG. 1A being a end view;

FIG. 4 is an exploded, side view of the cartridge assembly of the present invention and the drug cartridge and the corresponding portion of the pen shown in FIG. 3;

FIG. 5 is a partial, cross-sectional view of the cartridge assembly shown in FIG. 4 assembled;

FIG. 7 is a partial, cross-sectional view of another alternative embodiment of the cartridge assembly of the present invention;

DETAILED DESCRIPTION OF THE PREFERRED EMBODIMENT(S)

Figure 2:
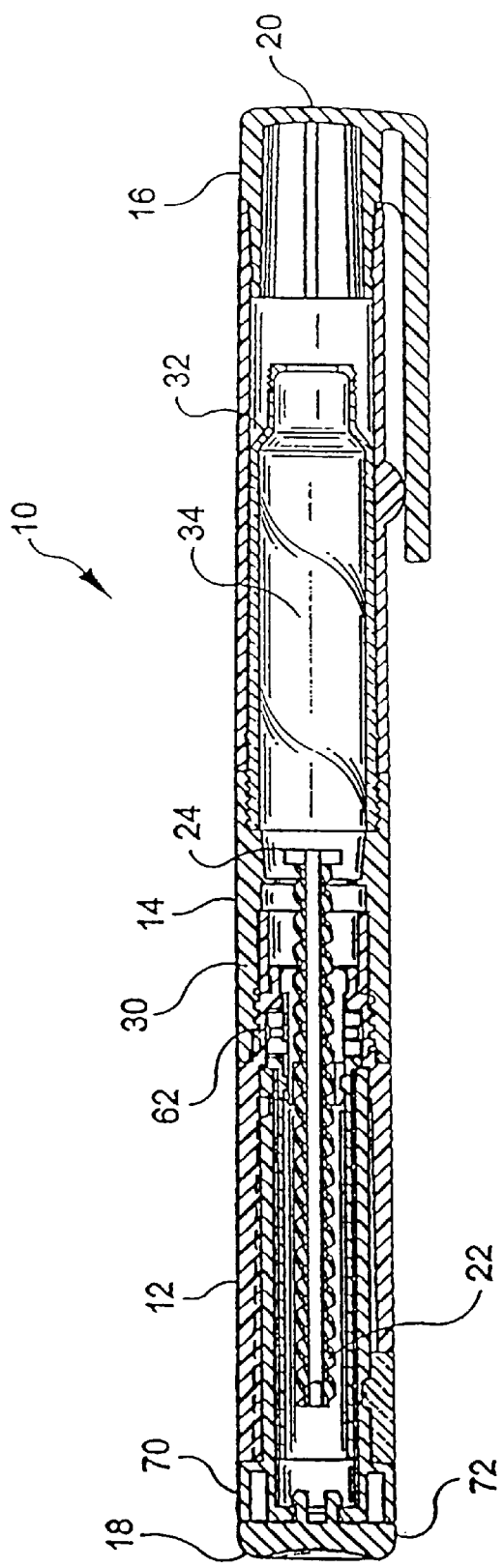
FIG. 2 is a cross-sectional view of the injection pen shown in FIG. 1 with the lead screw retracted.
Figure 3:
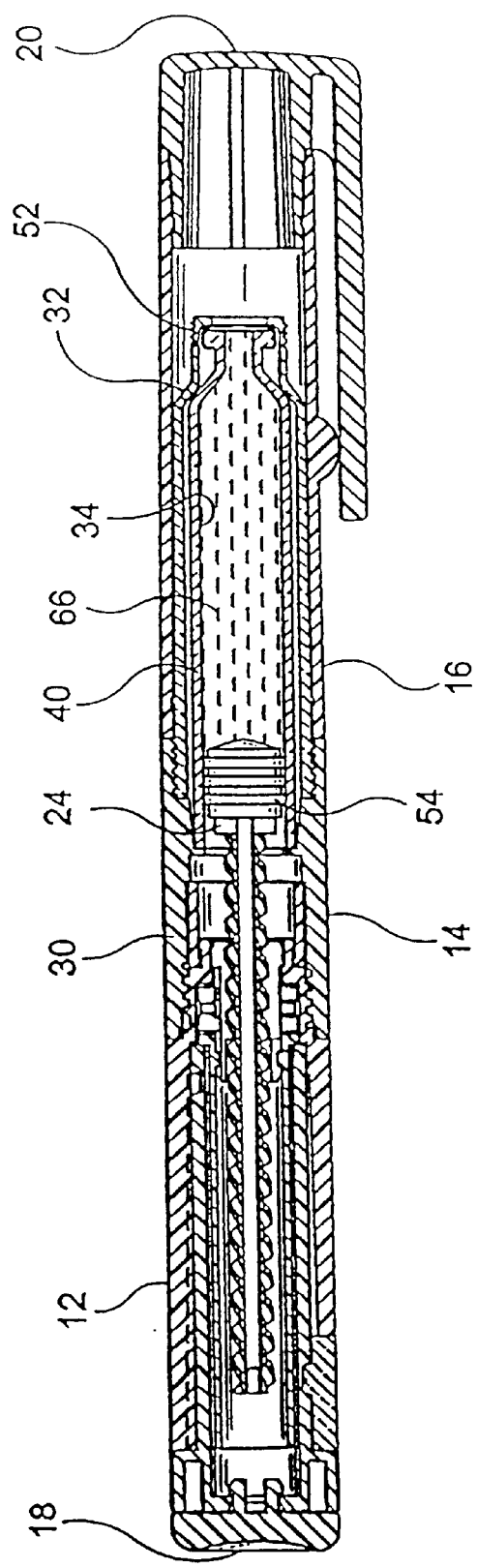
FIG. 3 is a partial, cross-sectional view of the injection pen similar to FIG. 2 with the lead screw retracted and a drug vial retained therein.

The medication delivery pen of the present invention is illustrated in FIGS. 1 through 5, with the pen being generally designated 10. As shown in FIGS. 1–3, the pen includes a pen body assembly 12, a cartridge assembly 14 an a cap 16, with the cartridge assembly being situated between the body assembly and the cap 16 and typically having sufficient medication for several doses. The pen body assembly and the cartridge assembly are keyed, i.e., they have a connection interface which mechanically prevents the cross-use of cartridges among designated pens by, for example, threadedly engaged by corresponding threads and grooves, bayonet threads and projecting tabs, snap fits or a pair of lugs that mate in a reverse Luer-lock manner. In addition, all of these elements have a generally cylindrical configuration and are arranged coaxially from opposed proximal and distal ends 18 and 20 of the pen 10 respectively to define a generally cylindrical housing which can easily be handled by a patient or medical attendant.

Referring to FIGS. 1 and 2, and in greater detail in FIG. 3, the body assembly 12 is used to set a desired dose of medication to be delivered by the pen 10 and includes an advancing member preferably in the form of a lead screw 22 with a distal end 24 movable in the distal direction based on the dose set by a dose setting mechanism within the pen body 12. The dose setting mechanism determines the distance through which lead screw 22 is to be moved during the injection of medication by the pen 10. It is understood, however, that variations from this preferred embodiment may be provided, and are considered to be within the scope of the subject invention. Particularly, the specific construction of the pen body 12, including the mechanisms for advancing the lead screw, may include those, for example, disclosed in U.S. Pat. Nos. 5,279,585 (Balkwill), 5,279,586 (Balkwill), 5,549,575 (Giambattista et al.), 5,569,214 (Chanoch), 5,582,598 (Chanoch), 5,645,534 (Chanoch), and 5,725,508 (Chanoch et al.), the disclosures of which are hereby incorporated by reference in their entirety. Accordingly, the particular pen body is not essential to the present invention and is merely a matter of choice.

As shown in FIGS. 1–3, and in greater detail in FIGS. 4 and 5, the cartridge assembly 14 is divided into two parts, i.e., an upper vial retainer 30 and a lower vial retainer 32, with the lower vial retainer defining a vial retaining cavity 34 formed in the lower vial retainer 32. As explained further herein, one end 36A of the upper vial retainer 30 is preferably dimensioned and configured to threadedly engage one end 38A of the lower vial retainer 32 and the other end 38B of the lower vial retainer 32 is configured to securely but releasably engage a needle cannula assembly (not shown). The particular needle cannula assembly is not essential to the present invention and may include the type disclosed in U.S. Pat. No. 5,931,817, the disclosure of which is hereby incorporated by reference in its entirety. The upper and lower retainers 30, 32 both are described in greater detail below.

The cartridge assembly 14, as shown in FIGS. 3, 4 and 5, includes a drug vial or cartridge 40, with the cavity 34 dimensioned and configured to securely receive and retain the drug cartridge therein. The drug cartridge 40 includes a generally tubular barrel 42 with a proximal end 44A defined by an inwardly converging shoulder 46 and an open distal end 44B. A smaller diameter neck 48 projects distally from the shoulder 46 of the barrel 42, and is provided with a large diameter annular bead (not shown) extending circumferentially thereabout at the extreme distal end of the neck. A pierceable and resealable elastomeric seal or septum 50 is securely mounted across the open distal end defined by the neck 48. The seal 50 is held in place by a metallic sleeve 52 which is crimped around the circumferential bead at the distal end of the neck 48. Medication is pre-filled into the drug cartridge 40 and is retained therein by an elastomeric stopper or plunger 54. The plunger 54 is in sliding fluid-tight engagement with the tubular wall of the barrel 42. Distally directed forces on the plunger 54 urge the medication from the pen as explained further below.

The portion of the lower retainer 32 defining the cavity 34 is of substantially uniform diameter which is slightly greater than the diameter of the vial barrel 42. The interior of the upper vial retainer 30 includes an inwardly-extending annual portion or stop 60 dimensioned to prevent the drug cartridge 40 from moving within the vial retainers 30, 32. In this way, when the drug cartridge 40 is inserted into the cavity 34 and the vial retainers 30, 32 threadedly engaged, the drug cartridge 40 is securely held in the cavity 34 at the open distal end 44B of the tubular barrel 42 by the annual stop 60. More particularly, the neck 48 and crimped metallic sleeve 52 of the drug cartridge 40 are inserted in a proximal to distal direction into the open proximal end of the lower retainer 32 with the crimped metallic sleeve 52 eventually passing entirely into the lower retainer 32, which will require entry of the crimped metallic sleeve into the portion thereof for mounting the needle cannula assembly. Then, with the vial retainers 30, 32 threadedly engaged, the open proximal end 44A of the drug vial 40 abuts the stops 60 of the upper vial retainer 30.

Preferably, when using standard drug vials or cartridges 40, the vial retainers 30, 32 are permanently secured to one another by glue, locking threads or other fastening means. In this way, the cartridge assembly 14 with the drug vial 40 secured therein may disposed of after being used.

The pen body assembly 12 includes an array of threads 62 for threaded engagement with the threaded other end 36B of the upper vial retainer 30, and when threadedly engaged, the plunger 54 is disposed in sliding fluid tight engagement in the cartridge assembly 40. As shown in FIG. 3, the lead screw 22 initially is disposed substantially adjacent the plunger 54 of the drug cartridge 40. The portion of drug cartridge 40 between the plunger 54 and the seal 50 is filled with a medication 66. In this way, advancement of the plunger 54 causes the medication 66 to be forced from the drug cartridge 40 through the needle cannula.

Preferably, the pen body assembly 12 is reusable and the drug cartridge 40 in the cartridge assembly 14 will contain a volume of medication 66 sufficient for administration of several doses. After exhaustion of the medication 66, the cartridge assembly 14 will be threadedly disengaged from pen body assembly 12 and the drug cartridge 40 discarded. A new assembly containing a drug cartridge may then be mounted to the reusable pen body assembly 12.

The assembled reusable pen body assembly 12 and cartridge assembly 14 may be stored until a selected dose of medication is required. Just prior to use, a needle cannula assembly may be threadedly engaged to distal end 38B of cartridge assembly 14. This threaded engagement will cause a proximal tip of a needle cannula to the pierce the seal 50 and provide communication with medication 66.

A desired dose of medication may be set by rotating a dose knob 70 located at the proximal end 18 of the pen which will cause advancement of the lead screw 22 into the cavity 34 of the cartridge assembly 14. When the desired dose is set, injection is achieved by merely pushing on actuator button 72 and the lead screw 22 will be advanced axially into cartridge assembly 14. This axial advancement of lead screw 22 causes distal end 24 thereof to come in contact with the plunger 54 and urge the plunger distally into the drug cartridge 40, and hence causes the medication 66 to be injected through the needle cannula. Injection will be terminated when the dose knob 70 is fully depressed into engagement with the pen body assembly 12.

Upon completion of the injection, the needle cannula assembly may be disengaged from the cartridge assembly 14 and safely discarded. The cap 16 may be mounted over cartridge assembly 14, and the pen 10 may be stored or carried in a convenient location until the next dose of medication is required. A subsequent dose of medication will be set in exactly the manner as described above. However, for such a subsequent dose, the plunger 54 will be in a partly advanced position as a starting point. Dose setting and injections can be carried out until all of medication 66 has been used. The cartridge assembly 14 may then be threadedly disengaged from pen body assembly 12, and slidably separated from the lead screw 22 and discarded in order to be replaced as described above.

Figure 6:
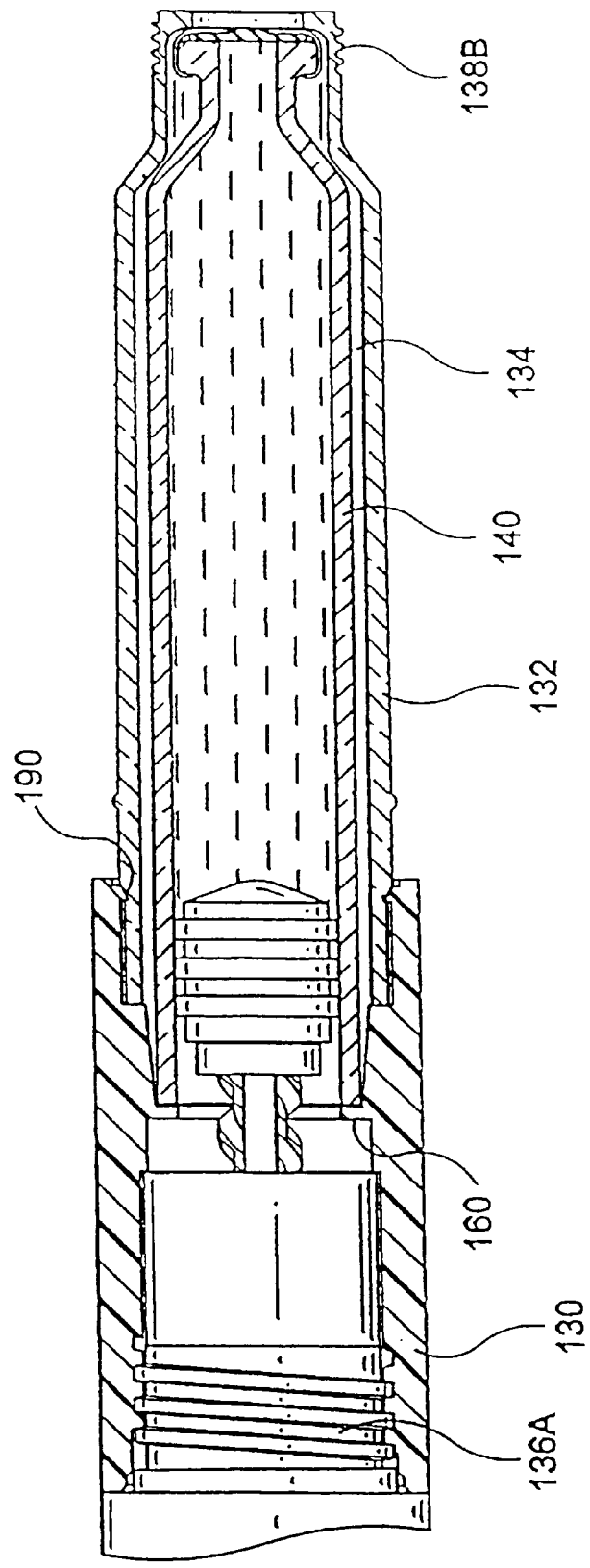
FIG. 6 is a partial, cross-sectional view of an alternative embodiment of the cartridge assembly of the present invention.

FIG. 6 shows an alternative embodiment of the cartridge assembly 114 which is disposable and includes an upper vial retainer 130 and a lower vial retainer 132. In this embodiment, once a drug cartridge 140 is placed in the cavity 134, the vial retainers 130, 132 are permanently secured to one another by glue or other fastening means 190. In this way, upon utilization of the medication, the drug cartridge assembly 114 along with the empty drug cartridge 140 may be disengaged from the pen body assembly and safely discarded.

FIG. 7 shows another alternative embodiment of the cartridge assembly 214 which is disposable and is in the form of a single integral unit having a generally tubular barrel 242 with a proximal end 244A defined by an inwardly converging shoulder 246 and an open distal end 244B. A smaller diameter neck 248 projects distally from the shoulder 246 of the barrel 242, and is provided with a pierceable and resealable elastomeric seal or septum 250 securely mounted across the open distal end defined by the neck 248. Medication is pre-filled into the integral cartridge assembly 214 and is retained therein by an elastomeric stopper or plunger 254. The plunger 254 is in sliding fluid-tight engagement with the tubular wall of the barrel 242. Distally directed forces on the plunger 254 urge the medication from the pen as explained interconnection with the preferred embodiment. In this embodiment, the distal end 244B of the integral cartridge assembly 214 include bayonet threads 280 which are engageable with corresponding projecting tab 282 formed in the distal end of the pen body 212. The distal end 244A of the tubular barrel is configured to securely but releasably engage a needle cannula assembly (not shown).

The cartridge assembly 214 shown in FIG. 7 may be assembled and pre-filled by any suitable means, including those disclosed, for example, in U.S. Pat. Nos. 5,279,585 (Balkwill), 5,531,255 (Vacca), 5,519,984 (Veussink et al.), 5,373,684 (Vacca), 5,207,983 (Liebert et al.), 4,718,463 (Jurgens, Jr. et al.), and 4,628,969 (Jurgens, Jr. et al.), and PCT Application No. WO 94/13328 (Hagen), the disclosures of which are hereby incorporated by reference in their entirety.

Figure 8:
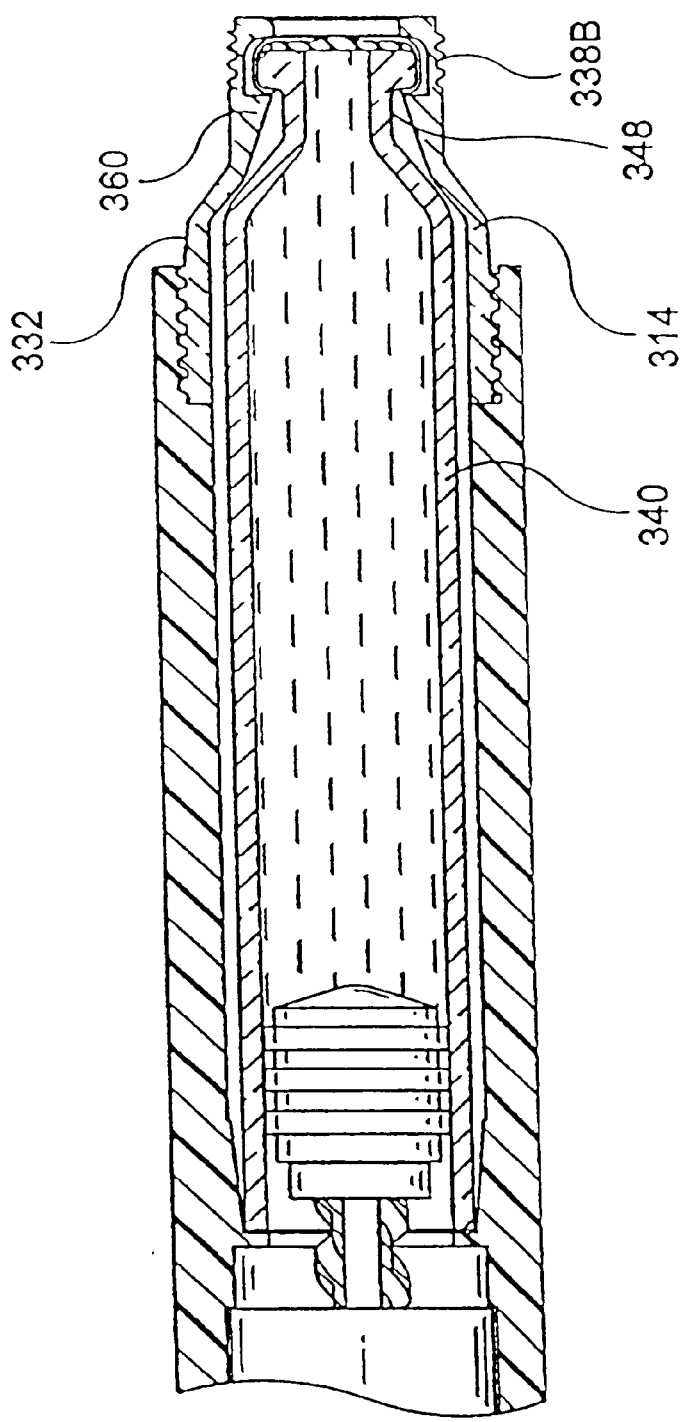
FIG. 8 is a partial, cross-sectional view of yet another alternative embodiment is of the cartridge assembly of the present invention.

FIG. 8 shows yet another alternative embodiment of the cartridge assembly 314 which is disposable and includes single vial retainer 332. However, a stop has been situated in the distal end 338B of the vial retainer 332 which permit the drug cartridge 340 to be inserted into the cavity 334 in one direction but resists removal of the drug cartridge, i.e., the insertion force is less than the removal force. Specifically, protrusions 360 project inwardly and extend along the neck 348 of the drug cartridge 40 to securely retain it in the cartridge assembly. In this way, upon utilization of the medication, the drug cartridge assembly 314 along with the empty drug cartridge 340 may be disengaged from the pen body assembly and safely discarded.

Figure 9:
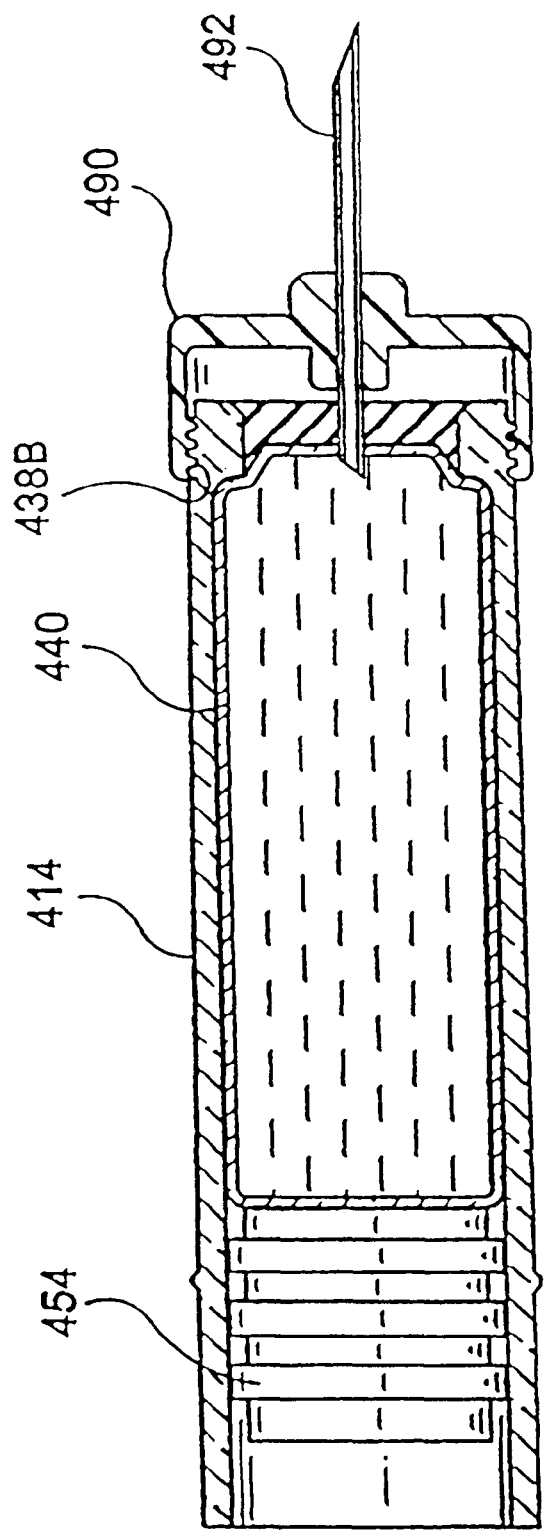
FIG. 9 is a partial, cross-sectional view of yet another alternative embodiment of the cartridge assembly of the present invention.

FIG. 9 shows yet another alternative embodiment of the cartridge assembly 414 which is disposable and includes single vial retainer in which a flexible vial or drug container 440 such as a pouch can be inserted into the cartridge assembly. Attached by treads or the like to the end 438B of the cartridge assembly is a cannula 490 having a double ended needle 492. In this way, upon movement of the plunger or stopper 454, the proximal end of the needle 492 pierces the drug container to permit the drug to be released therefrom as the container collapses.

The particular material of which the cartridge assembly is made is not essential to the present invention but preferably includes a polymeric material such as polycarbonate. However, the particular material is a matter of choice depending upon availability, the manufacturing process used and the intended use of the cartridge assembly. For example, where the cartridge assembly 214 is pre-filled with the medication, the polymeric material must be compatible with the medication contained therein.

It should be appreciated from the detailed description of the preferred embodiments, that the particular means by which the pen body assembly 12 and the cartridge assembly are keyed, i.e., engaged so as to reduce or otherwise eliminate cross-use is essential and may be threadedly engaged by corresponding threads and grooves, bayonet threads and grooves, snap fits or a pair of lugs that mate in a reverse Luer-lock manner. In this way, the pen body assembly 12 includes either a female or male mating member and the cartridge assembly 14 includes a corresponding female or male mating member engageable with one another for interconnecting the two assemblies, with the mating members selected so as to prevent cross-use with other assemblies, e.g., the pitch of the threads may be angled so as to mate only with one another and not with other assemblies.

Also, the cartridge holder sleeve can have an embedded cartridge, not readily separable from each other as described in connection with one alternative embodiment. In addition, the drug cartridge can be designed as a single integral unit for containing the drug as described in connection with another alternative embodiment.

While the preferred embodiments of the present invention have been described so as to enable one skilled in the art to practice the device of the present invention, it is to be understood that variations and modifications may be employed without departing from the concept and intent of the present invention as defined in the following claims. The preceding description is intended to be exemplary and should not be used to limit the scope of the invention. The scope of the invention should be determined only by reference to the following claims.

What is claimed is:

1. A medication delivery pen comprising:
    a drug cartridge including:
        a generally tubular barrel having a distal end and an open proximal end, with a chamber defined by a tubular wall of said barrel extending between said distal end and said proximal end;
        sealing means located on with said distal end of said tubular barrel for sealing said distal end of said tubular barrel; and,
        plunger means located on with said open proximal end of said tubular barrel in sliding fluid-tight engagement with said tubular wall of said barrel for selective engagement with an advancing member so that distally directed forces on said plunger urge a medication pre-filled in said chamber from said drug cartridge;
    a pen body assembly adapted to be releasably interconnected to said drug cartridge, said pen body having proximal and distal ends; and
    mating means for releasably interconnecting said drug cartridge with said pen body assembly, said mating means including at least one bayonet thread having a substantially U-shaped configuration with a closed bottom and at least one projecting tab, said bayonet thread being associated with one of said proximal end of said tubular barrel and said distal end of said pen body assembly, and said tab being located on with, and located to be wholly spaced from, the other end of said proximal end of said tubular barrel and said distal end of said pen body assembly such that said tab is accommodated within said U-shaped configuration of said bayonet thread with said closed bottom extending transversely to said tab to inhibit movement of said tab when said drug cartridge is interconnected to said pen body assembly.

2. The pen of claim 1 wherein said distal end of the tubular barrel is configured to securely but releasably engage a needle cannula assembly.

3. The pen of claim 1 wherein said generally tubular barrel is made of a polymeric material.

4. The pen of claim 1 further comprising a medication contained in said chamber.

5. A medication delivery pen comprising:
    a drug cartridge including:
        a generally tubular barrel made of a polymeric material having a distal end and an open proximal end, with a chamber defined by a tubular wall of said barrel extending between said distal end and said proximal end;
        sealing means associated with said distal end of said tubular barrel for sealing said distal end of said tubular barrel;
        an elastomeric plunger associated with said open proximal end of said barrel in sliding fluid-tight engagement with said tubular wall of said barrel; and,
        medication contained in said chamber and retained therein by said sealing means and said plunger so that distally directed forces on said plunger urge said medication from said drug cartridge;
    a pen body assembly adapted to be releasably interconnected to said drug cartridge, said pen body having proximal and distal ends; and
    mating means for releasably interconnecting said drug cartridge with said pen body assembly, said mating means including at least one bayonet thread having a substantially U-shaped configuration with a closed bottom and at least one projecting tab, said bayonet thread being located on with one of said proximal end of said tubular barrel and said distal end of said pen body assembly, and said tab being associated with, and located to be wholly spaced from, the other of said proximal end of said tubular barrel and said distal end of said pen body assembly such that said tab is accommodated within said U-shaped configuration of said bayonet thread with said closed bottom extending transversely to said tab to inhibit movement of said tab when said drug cartridge is interconnected to said pen body assembly.

6. The pen of claim 5 wherein said distal end of the tubular barrel is configured to securely but releasably engage a needle cannula assembly.

7. The pen of claim 5 wherein said medication is contained within a flexible container and a needle cannula attached to the distal end of the tubular barrel with said cannula included a double ended needle so that one end of said double ended needle can pierce said flexible container.

* * * * *

UNITED STATES PATENT AND TRADEMARK OFFICE
CERTIFICATE OF CORRECTION

PATENT NO.      : 6,648,859 B2                                              Page 1 of 1
DATED           : November 18, 2003
INVENTOR(S)     : Bitdinger et al.

It is certified that error appears in the above-identified patent and that said Letters Patent is hereby corrected as shown below:

<u>Column 3,</u>
Line 50, delete "...embodiment is of the cartridge..." and insert -- embodiment of the cartridge --.

<u>Column 4,</u>
Line 50, delete "...with a proximal end 44A..." and insert -- with a distal end 44B --.
Lines 51-52, delete "...an open distal end 44B..." and insert -- an open proximal end 44A --.

<u>Column 5,</u>
Lines 7-8, delete "... the open distal end 44B..." and insert -- the open proximal end 44A --.

<u>Column 6,</u>
Line 24, delete "...with a proximal end 244A..." and insert -- with a distal end 244B --.
Line 25, delete "...an open distal end 244B..." and insert -- an open proximal end 244A --.
Line 35, delete "...explained interconnection with..." and insert -- explained in connection with --.
Line 36, delete "...the distal end 244B..." and insert -- the proximal end 244A --.
Lines 39-40, delete "...The distal end 244A..." and insert -- The distal end 244B --.

<u>Column 7,</u>
Line 53, delete "...located on with said distal..." and insert -- located on said distal --.
Line 56, delete "...located on with..." and insert -- located on --.

<u>Column 8,</u>
Line 6, delete "...being located on with,..." and insert -- being located on, --.
Line 47, delete "...being located on with one..." and insert -- being located on one --.

Signed and Sealed this

Seventeenth Day of February, 2004

JON W. DUDAS
*Acting Director of the United States Patent and Trademark Office*